United States Patent
Fukumoto

(10) Patent No.: US 12,148,600 B2
(45) Date of Patent: Nov. 19, 2024

(54) DEPOSITION-CONDITION OUTPUT DEVICE, METHOD FOR OUTPUTTING DEPOSITION CONDITION, RECORDING MEDIUM AND DEPOSITON APPARATUS

(71) Applicant: Tokyo Electron Limited, Tokyo (JP)

(72) Inventor: Toshiyuki Fukumoto, Yamanashi (JP)

(73) Assignee: Tokyo Electron Limited, Tokyo (JP)

( * ) Notice: Subject to any disclaimer, the term of this patent is extended or adjusted under 35 U.S.C. 154(b) by 416 days.

(21) Appl. No.: 17/380,253

(22) Filed: Jul. 20, 2021

(65) Prior Publication Data

US 2022/0037134 A1 Feb. 3, 2022

(30) Foreign Application Priority Data

Aug. 3, 2020 (JP) .................................. 2020-131867

(51) Int. Cl.
*C23C 14/54* (2006.01)
*C23C 16/52* (2006.01)
(Continued)

(52) U.S. Cl.
CPC ........ *H01J 37/32926* (2013.01); *C23C 16/52* (2013.01); *G06N 20/20* (2019.01);
(Continued)

(58) Field of Classification Search
USPC .......................................................... 700/30
See application file for complete search history.

(56) References Cited

U.S. PATENT DOCUMENTS

2012/0084063 A1 * 4/2012 Drees ................... G05B 13/048
703/6
2018/0356807 A1 * 12/2018 Honda ............. G05B 19/41885
(Continued)

FOREIGN PATENT DOCUMENTS

| JP | 2003-166066 | 6/2003 |
| JP | 2007-287153 | 11/2007 |
| JP | 6647473 | 2/2020 |

OTHER PUBLICATIONS

Mitchell., "Machine Learning" McGraw-Hill, 1997, 421 pages (Year: 1997).*

*Primary Examiner* — Emilio J Saavedra
(74) *Attorney, Agent, or Firm* — IPUSA, PLLC

(57) ABSTRACT

A deposition-condition output device includes a first calculating unit that calculates a first deposition condition under which a target result of deposition is obtained, based on a liner regression model applied to a deposition process by a deposition apparatus. The deposition-condition output device includes a second calculating unit that calculates a second deposition condition under which the target result of the deposition is obtained, based on a nonlinear regression model applied to the deposition process by the deposition apparatus, the second deposition condition being calculated by estimating a confidence interval of a predicted result of the deposition. The deposition-condition output device includes a selector that selects either the first deposition condition or the second deposition condition, based on whether the confidence interval of the predicted result estimated under the calculated second deposition condition satisfies a predetermined condition.

8 Claims, 12 Drawing Sheets

(51) Int. Cl.
*G06N 20/20* (2019.01)
*H01J 37/32* (2006.01)
*G05B 19/418* (2006.01)
*G06N 20/00* (2019.01)
*G16C 20/70* (2019.01)

(52) U.S. Cl.
CPC ...... *C23C 14/542* (2013.01); *G05B 19/41885* (2013.01); *G06N 20/00* (2019.01); *G16C 20/70* (2019.02)

(56) References Cited

U.S. PATENT DOCUMENTS

2020/0051235 A1\* 2/2020 Majumdar .............. H01L 22/12
2022/0012641 A1\* 1/2022 Iyengar ................... G06F 18/22

\* cited by examiner

DEPOSITION-CONDITION OUTPUT DEVICE, METHOD FOR OUTPUTTING DEPOSITION CONDITION, RECORDING MEDIUM AND DEPOSITON APPARATUS

CROSS-REFERENCE TO RELATED APPLICATION

This patent application claims priority to Japanese Patent Application No. 2020-131867, filed Aug. 3, 2020, the contents of which are incorporated herein by reference in their entirety.

TECHNICAL FIELD

The present disclosure relates to a deposition-condition output device, a method for outputting a deposition condition, a recording medium, and a deposition apparatus.

BACKGROUND

For deposition apparatuses, various prediction models have been proposed in order to search for optimal deposition conditions under which target results of deposition are obtained. In the prediction models, deposition processes by the deposition apparatuses are modeled using machine learning. The prediction model includes, for example, a nonlinear regression model.

Nonlinear regression models are more flexible than linear regression models, and even when the model output obeys a complicated regression curve, prediction accuracy can be locally increased. However, global prediction accuracy may be decreased due to biased samples, a shortage of samples, or the like. For this reason, when the deposition process is performed under a deposition condition optimized using a nonlinear regression model, the actual result of the deposition may deviate greatly from the anticipated deposition result.

CITATION LIST

Patent Document

Patent document 1: Japanese Patent No. 6647473

SUMMARY

According to one aspect of the present disclosure, a deposition-condition output device includes a processing circuit. The processing circuit is configured to calculate a first deposition condition under which a target result of deposition is obtained, based on a liner regression model applied to a deposition process by a deposition apparatus. The processing circuit is configured to calculate a second deposition condition under which the target result of the deposition is obtained, based on a nonlinear regression model applied to the deposition process by the deposition apparatus, the second deposition condition being calculated by estimating a confidence interval of a predicted result of the deposition. The processing circuit is configured to determine whether the confidence interval of the predicted result estimated under the calculated second deposition condition satisfies a predetermined condition. The processing circuit is configured to select one from among the first deposition condition and the second deposition condition, based on whether the confidence interval satisfies the predetermined condition.

DETAILED DESCRIPTION

One or more embodiments will be described with reference to the drawings. Note that in each drawing, the same numerals denote the same or substantially same components, and duplicate description for the components will be omitted.

First Embodiment

Example of Application of Deposition-Condition Output Device

Figure 1:
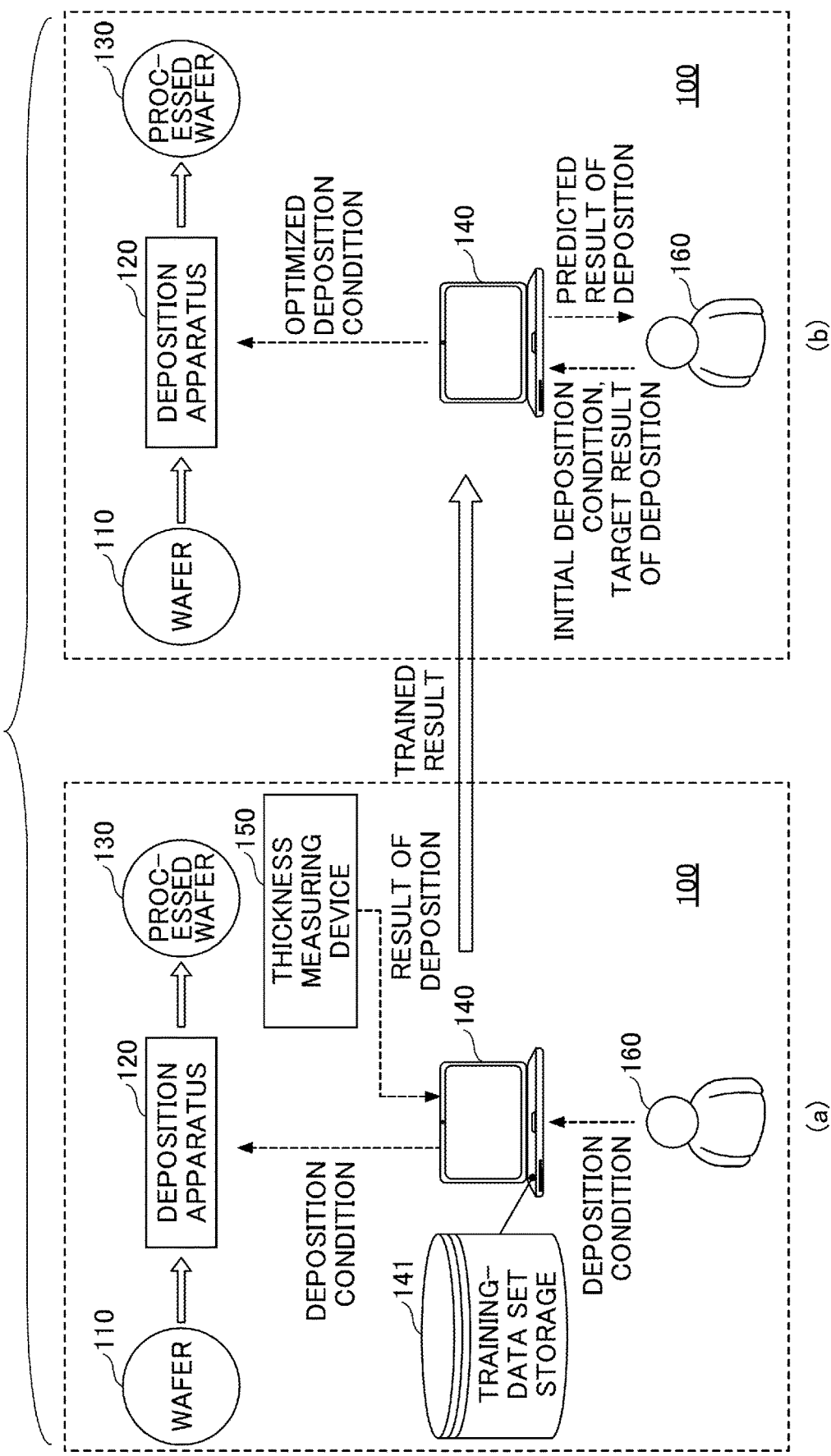
FIG. 1 is a diagram illustrating an example of how a deposition-condition output device may be applied.

An example of the application of a deposition-condition output device according to a first embodiment will be described. FIG. 1 is a diagram illustrating the example of how the deposition-condition output device may be applied. FIG. 1(a) illustrates an example of how the deposition-condition output device is applied in a training phase.

As illustrated in FIG. 1(a), in the training phase, a deposition system 100 includes a deposition apparatus 120, a deposition-condition output device 140, and a thickness measuring device 150.

The deposition apparatus 120 performs a deposition process for an object (wafer 110) to thereby produce a result (processed wafer 130). In the present embodiment, the deposition apparatus 120 is described as, for example, a deposition apparatus with plasma sources, with which a single wafer is processed using each plasma source. However, the deposition apparatus 120 is not limited to the example described above. For example, the deposition apparatus 120 may be a deposition apparatus with a single plasma source, or may be a batch-type deposition apparatus that performs a deposition process for multiple wafers 110. Note, however, that when the batch-type deposition apparatus is used, in a case where the deposition-condition output device 140 performs the process described below in each process zone, respective processes are simultaneously performed in all process zones.

Note that the wafer 110 refers to a wafer (substrate) before the deposition process is performed in the deposition apparatus. The processed wafer 130 refers to a wafer (substrate) after the deposition process is performed in the deposition apparatus.

The thickness measuring device 150 measures a thickness of the wafer 110 at each point, and measures a thickness of the processed wafer 130 at each point. The thickness measuring device 150 also transmits, as a result of deposition, thicknesses measured at points of each of the wafer 110 and the processed wafer 130, to the deposition-condition output device 140. Note that in the present embodiment, as an example of the result of the deposition, the thickness measured at each position by the thickness measuring device 150 is transmitted to the deposition-condition output device 140. However, the result of the deposition to be transmitted to the deposition-condition output device 140 is not limited to the thickness at each position. For example, instead of (or in addition to) the thickness at each position, film quality at each position may be transmitted.

In response to receiving a deposition condition that is input by a user 160, the deposition-condition output device 140 sets the deposition condition in the deposition apparatus 120. The deposition-condition output device 140 also acquires the result of the deposition measured under the set deposition condition at which the deposition process is performed in the deposition apparatus 120.

The deposition-condition output device 140 generates a plurality of pieces of training data each including the set deposition condition and the acquired result of the deposition. The generated pieces of training data are stored, as a training data set, in the training-data set storage 141. Further, the deposition-condition output device 140 reads out the stored training data set, performs a training process for each of prediction models (a linear model and a non-linear regression model) using the pieces of training data, and then outputs the trained results (trained prediction models).

FIG. 1(b) illustrates an example of how the deposition-condition output device is applied in the prediction phase. As illustrated in FIG. 1(b), in the prediction phase, the deposition system 100 includes the deposition apparatus 120 and the deposition-condition output device 140.

Note that in the present embodiment, the deposition apparatus 120 illustrated in FIG. 1(b) is described as the same apparatus as the deposition apparatus 120 in the training phase. However, the deposition apparatus in the training phase and the deposition apparatus in the prediction phase may be, for example, different apparatuses of the same type.

The deposition-condition output device 140 executes a plurality of trained prediction models (linear model and nonlinear regression model) based on an initial deposition condition and a target result of deposition, which are input by the user 160. The deposition-condition output device 140 also selects an optimized deposition condition and a predicted result of the deposition, from among executed results by the trained prediction models. Further, the deposition-condition output device 140 provides the user 160 with the selected optimized deposition condition and predicted result. Note that the optimized deposition condition is confirmed by the user 160 and then is set in the deposition apparatus 120.

Thus, a given optimized deposition condition selected from among the results executed by the trained prediction models is set in the deposition apparatus 120. Accordingly, an appropriately optimized deposition condition can be set.

Specifically, when prediction accuracy of the non-linear regression model is reduced due to biased data samples, a shortage of data samples, or the like, a given optimized deposition condition and predicted result of the deposition are selected based on results executed by the linear model. In addition, when prediction accuracy of the nonlinear regression model is increased, a given optimized deposition condition and predicted result of the deposition are selected based on results executed by the nonlinear regression model.

Thus, in the deposition apparatus 120, the processed wafer 130 can be provided to thereby achieve a given target result of the deposition.

<Hardware Configuration of Deposition-Condition Output Device>

Figure 2:
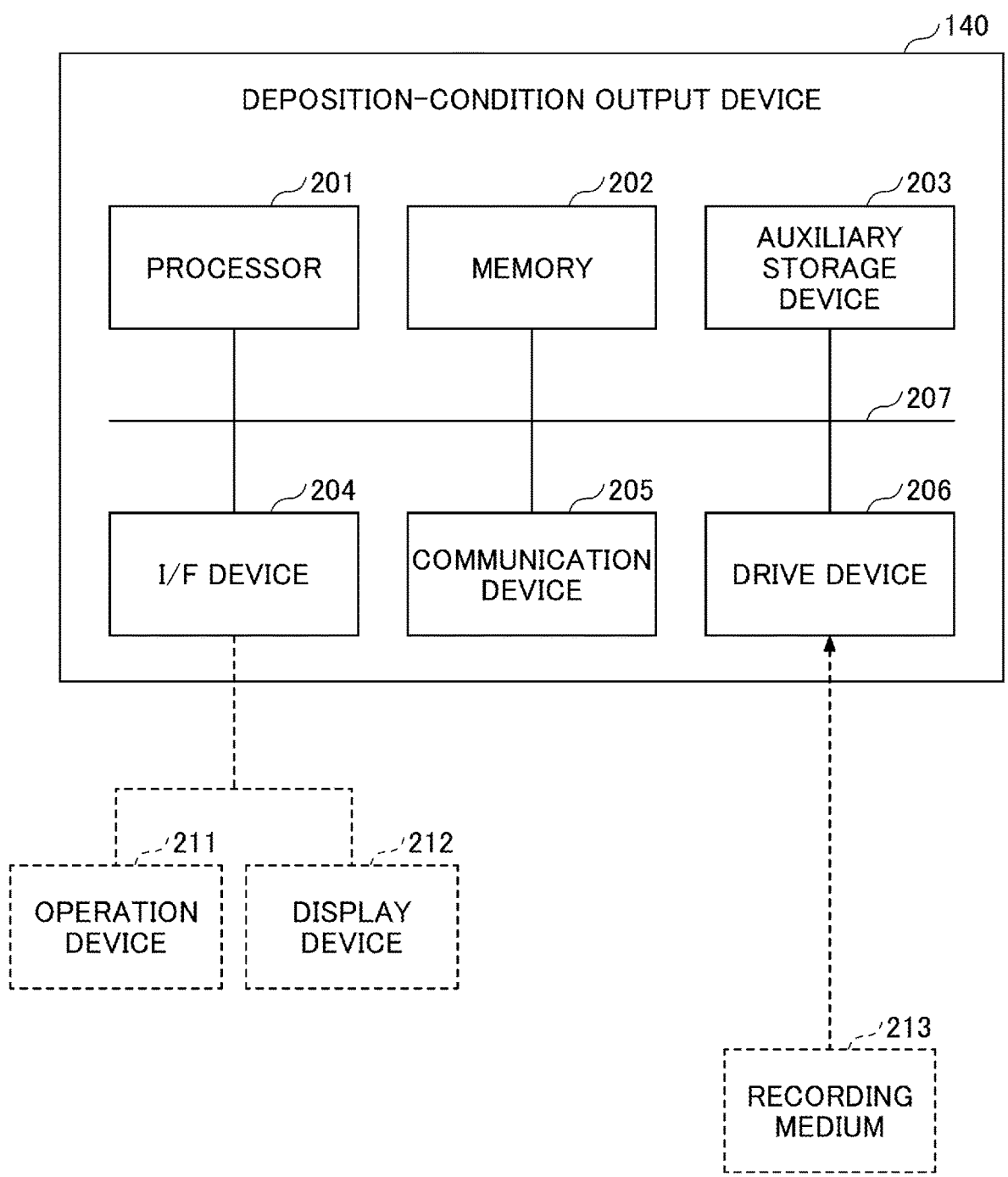
FIG. 2 is a diagram illustrating an example of the hardware configuration of the deposition-condition output device.

FIG. 2 is a diagram illustrating an example of the hardware configuration of the deposition-condition output device 140. As illustrated in FIG. 2, the deposition-condition output device 140 includes a processor 201, a memory 202, an auxiliary storage device 203, an interface (I/F) device 204, a communication device 205, and a drive device 206. Note that hardware components of the deposition-condition output device 140 are mutually coupled via a bus 207.

The processor 201 includes various arithmetic devices including a central processing unit (CPU), a graphics processing unit (CPU), and the like. The processor 201 reads one or more programs (for example, a program and the like that causes a computer to output a deposition condition, as described below) onto the memory 202, to thereby execute the programs.

The memory 202 includes a main storage such as a read only memory (ROM) or a random access memory (RAM). The processor 201 and the memory 202 are main components of a computer. When the processor 201 retrieves one or more programs from the memory 202 to thereby execute the programs, the computer implements various functions.

The auxiliary storage device 203 stores one or more programs and various data to be used when the processor 201 executes the programs. For example, the training-data set storage 141 is Implemented by the auxiliary storage device 203.

The I/F device 204 is used to interface with external devices such as an operation device 211, a display device 212, and the deposition-condition output device 140. The I/F device 204 receives an operation (for example, the input of a deposition condition, the input of an initial deposition condition, the input of a target result of deposition, or the like) associated with the deposition-condition output device 140, through the operation device 211. The I/F device 204 also outputs an executed result (for example, a predicted result of deposition, an optimized deposition condition, or the like) by the deposition-condition output device 140, and thus the display device 212 displays the executed result.

The communication device 205 is used to communicate with other devices (for example, deposition apparatus 120) via a network.

The drive device 206 is used to set a recording medium 213. The recording medium 213 includes a medium for optically, electrically, or magnetically recording information. For example, the medium may include a CD-ROM, a flexible disk, a magneto-optical disk, or the like. The recording medium 213 may also include a semiconductor memory or the like that electrically records information. For example, the semiconductor memory includes a read only memory (ROM), a flash memory, or the like.

Note that when a provided recording medium 213 is set in the drive device 206, and then one or more programs recorded in the recording medium 213 are retrieved by the drive device 206, the one or more programs may be installed in the auxiliary storage device 203. Alternatively, when one or more programs are downloaded via a network not illustrated, the one or more programs may be installed in the auxiliary storage device 203.

Specific Example of Training Data Set

Figure 3:
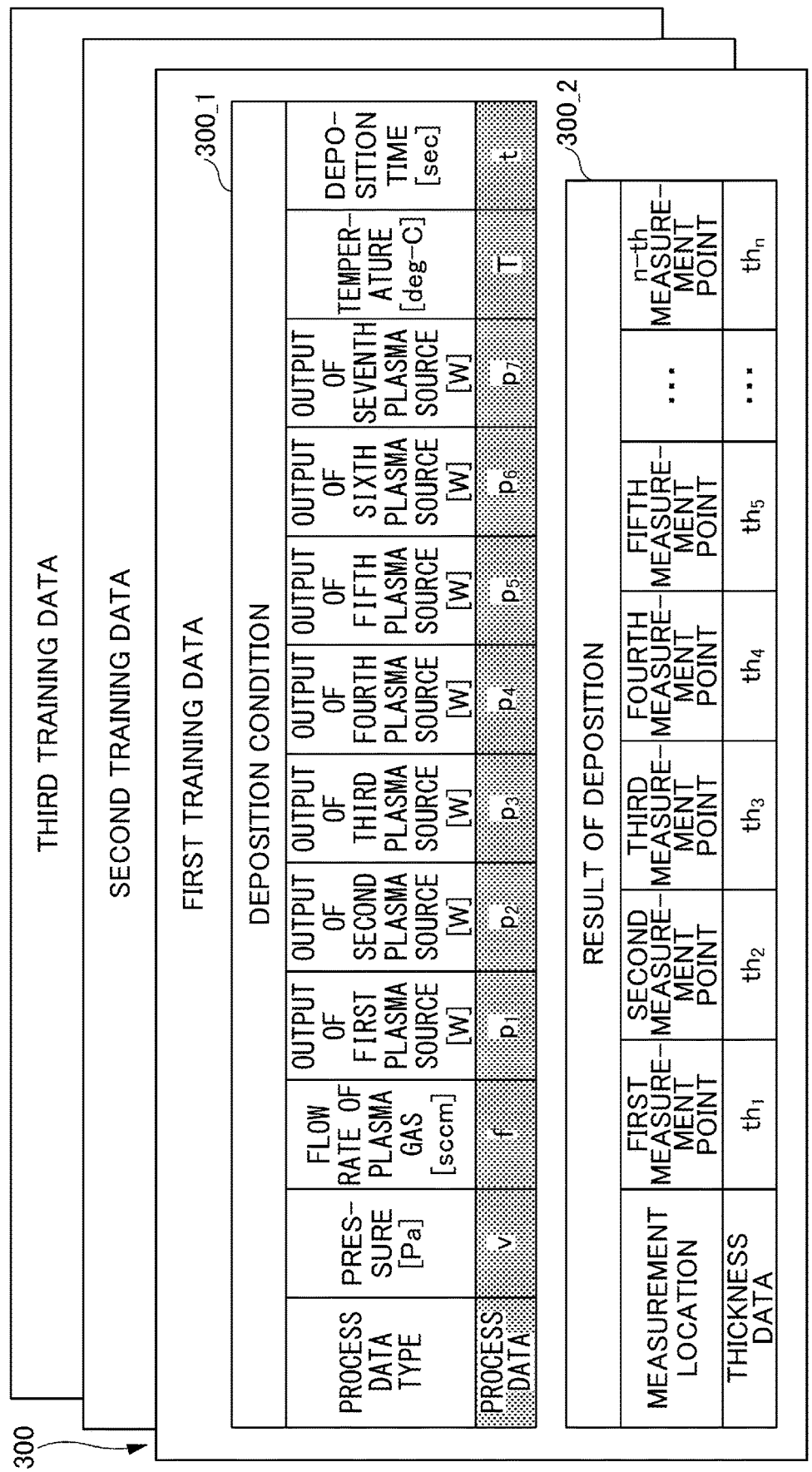
FIG. 3 is a diagram illustrating an example of a training data set stored in a training-data set storage.

Hereafter, a specific example of the training data set stored in the training-data set storage 141 will be described. FIG. 3 is a diagram illustrating an example of the training data set stored in the training-data set storage.

As illustrated in FIG. 3, a training data set 300 includes pieces of training data, such as first training data, second training data, and third training data. Each training data consists of a combination of a deposition condition and a result of deposition. In the example in FIG. 3, "first training data" consists of a combination of a deposition condition 3001 and a result 3002 of deposition.

As illustrated in FIG. 3, the deposition condition 3001 includes information items consisting of "process data type" and "process data."

The "process data type" relates to deposition. In the example in FIG. 3, the process data type includes "pressure", "flow rate of plasma gas", "output of first plasma source" to "output of seventh plasma source", "temperature", and "deposition time."

For the "process data," a value of process data is set in association with each of the "process data type."

Further, as illustrated in FIG. 3, the result 300_2 of deposition includes information items consisting of "measurement location" and "thickness data."

For the "measurement location," measurement points each specifying a location at which a thickness is measured by the thickness measuring device 150 are set, where the location is among locations on a given processed wafer 130. In the present embodiment, the thickness measuring device 150 measures respective thicknesses at n points. For the "thickness data", a value of measured thickness data is set in association with each measurement point of the "measurement location."

<Functional Configuration of Deposition-Condition Output Device>

Hereafter, the functional configuration of the deposition-condition output device 140 will be described with reference to FIG. 4 and FIG. 5.

(1) Deposition-Condition Output Device in Training Phase

Figure 4:
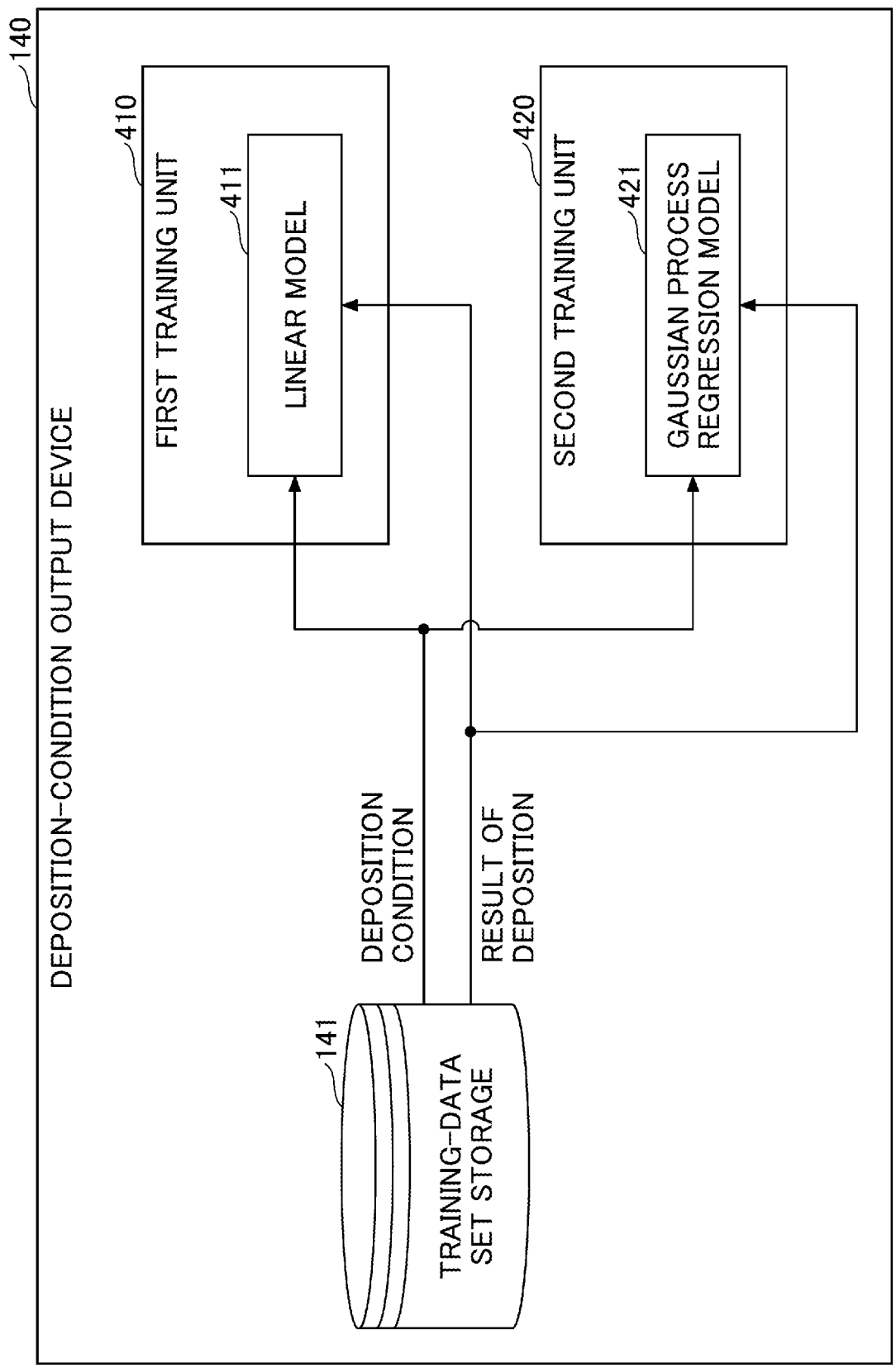
FIG. 4 is a diagram illustrating an example of the functional configuration of the deposition-condition output device in a training phase.

FIG. 4 is a diagram illustrating an example of the functional configuration of the deposition-condition output device in the training phase. As described above, when a given program to cause a computer to output a deposition condition is installed in the deposition-condition output device 140, and then the given program is executed in the training phase, the deposition-condition output device 140 serves as a first training unit 410 and a second training unit 420.

The first training unit 410 has a linear model 411. The first training unit 410 uses the training data set 300 retrieved from the training-data set storage 141, to thereby update model parameters of the linear model 411. Specifically, the first training unit 410 updates the model parameters such that, when a given deposition condition (for example, the deposition condition 3001) included in each training data is input into the linear model 411, the output of the linear model 411 approaches a result of the deposition (for example, the result 3002 of the deposition) included in corresponding training data. Note that a trained linear model (trained result) of which the model parameters are updated is used in the prediction phase.

The second training unit 420 has a Gaussian process regression model 421, which is an example of a nonlinear regression model. The Gaussian process regression model is a non-parametric probability model that can output a predicted result (in the present embodiment, a predicted result of the deposition) and variance (in the present embodiment, a width of a given confidence interval) of the predicted result.

In FIG. 4, the second training unit 420 uses the training data set 300 retrieved from the training-data set storage 141 to thereby update model parameters of the Gaussian process regression model 421. Specifically, the second training unit 420 updates the model parameters such that, when a given deposition condition (for example, deposition condition 3001) included in each training data is input into the Gaussian process regression model 421, the output of the Gaussian process regression model 421 approaches a result of the deposition (for example, the result 3002 of the deposition) included in corresponding training data. Note that a trained Gaussian process regression model (trained result) of which the model parameters are updated is used in the prediction phase.

For example, when the trained Gaussian process regression model generated in the prediction phase is expressed by Equation (1) below, the Gaussian process regression model used in the prediction phase can be expressed by Equation (2) below.

[Formula 1]

$$p(y \mid X) = N\left(0, \sum\nolimits^{(n)}\right) \quad (1)$$

[Formula 2]

$$p(y, y_{n+1} \mid X, x_{n+1}) = N\left(0, \begin{pmatrix} \sum^{(n)} & \sum_{n+1}^{(n)} \\ (\sum_{n+1}^{(n)})^T & \sum_{n+1} \end{pmatrix}\right) \quad (2)$$

Note that in Equations (1) and (2) above, X and y respectively represent a deposition condition and a result of the deposition, which are included in each training data used in the training phase. Also, $x_{n+1}$ and $y_{n+1}$ respectively represent a deposition condition and a result of the deposition, which are optimally calculated. Moreover, $\Sigma^{(n)}$ and $\Sigma_{n+1}$ are diagonal blocks of a covariance matrix of a Gaussian process. Where, an off-diagonal block of the covariance matrix in the Gaussian process is given as follows.

$$\Sigma_{n+1}^{(n)} \quad \text{[Formula 3]}$$

From Equation (2) above, a predicted value indicating the degree to which the deposition obeys a probability distribution expressed by Equation (3) below.

[Formula 4]

$$p(y_{n+1} \mid x_{n+1}, y, X) = N((\Sigma_{n+1}^{(n)})^T (\Sigma^{(n)})^{-1} y, \Sigma_{n+1} - (\Sigma_{n+1}^{(n)})^T (\Sigma^{(n)})^{-1} \Sigma_{n+1}^{(n)}) \quad (3)$$

From Equation (3) above, when the Gaussian process regression model generated in the training phase is used, a given result of the deposition obtained under a given deposition condition in which $x_{n+1}$ is set is given as follows.

$$(\Sigma_{n+1}^{(n)})^T (\Sigma^{(n)})^{-1} y \quad \text{[Formula 5]}$$

The result of the above representation is a mean for the right-hand side of the Gaussian distribution expressed by Equation (3) above. Moreover, in the Gaussian process regression model, when a given deposition condition is optimized, the deposition condition $x_{n+1}$ is calculated such that the mean of the Gaussian distribution approaches a given target result of the deposition. The mean of the Gaussian distribution is given as follows.

$$(\Sigma_{n+1}^{(n)})^T(\Sigma^{(n)})^{-1}y \qquad \text{[Formula 6]}$$

Moreover, when a given result of the deposition is predicted using the Gaussian process regression model 421, the confidence interval is calculated based on variance of the Gaussian distribution. The variance of the Gaussian distribution corresponds to the right-hand side of Equation (1) above, and is given as follows.

$$\Sigma_{n+1} - (\Sigma_{n+1}^{(n)})^T(\Sigma^{(n)})^{-1}\Sigma_{n+1}^{(n)} \qquad \text{[Formula 7]}$$

(2) Deposition-Condition Output Device in Prediction Phase

Figure 5:
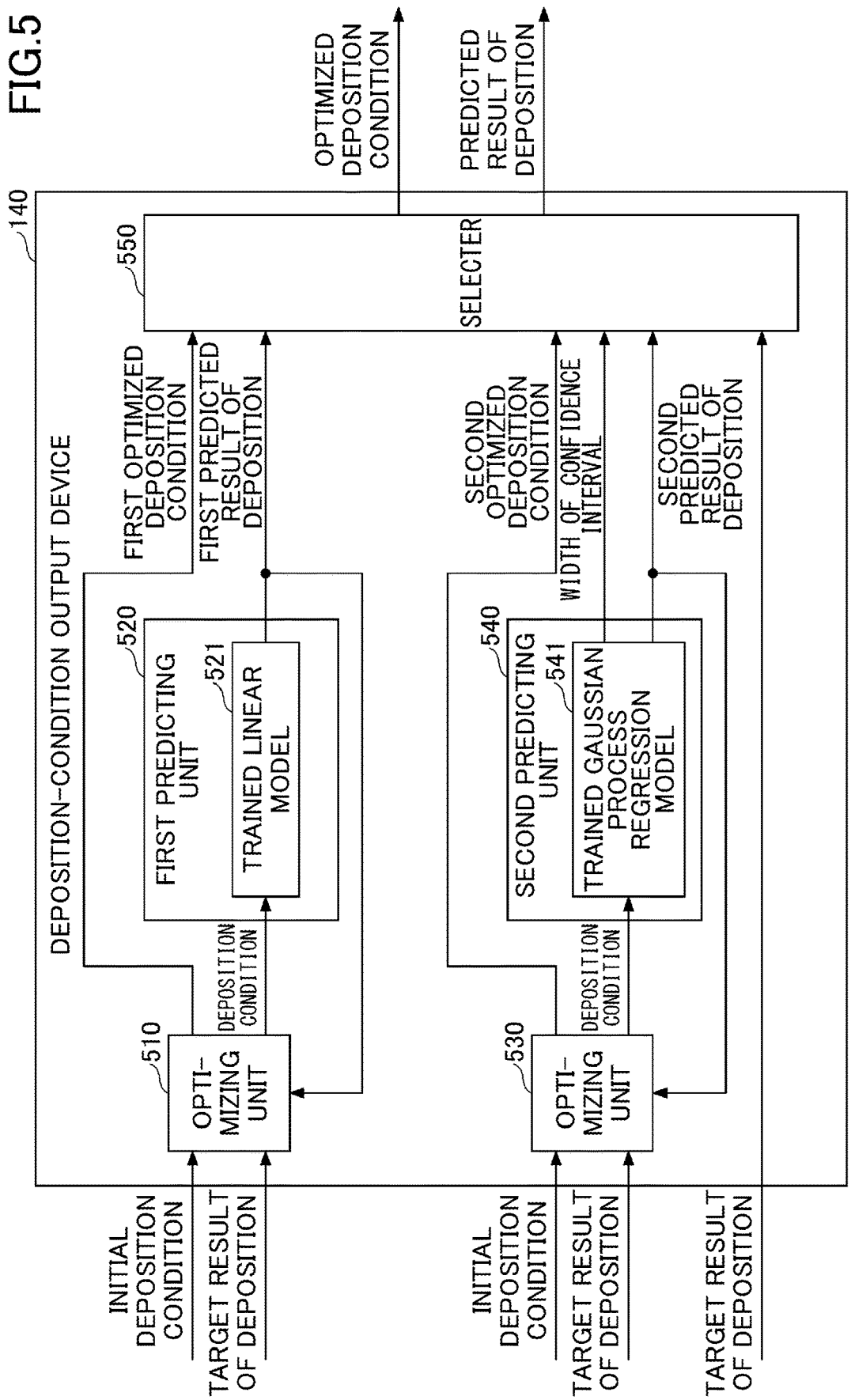
FIG. 5 is a diagram illustrating an example of the functional configuration of the deposition-condition output device in a prediction phase.

FIG. 5 is a diagram illustrating an example of the functional configuration of the deposition-condition output device in the prediction phase. As described above, a given program to cause a computer to output a deposition condition is installed in the deposition-condition output device 140. When the given program is executed in the prediction phase, the deposition-condition output device 140 serves as an optimizing unit 510, a first predicting unit 520, an optimizing unit 530, a second predicting unit 540, and a selector 550.

The optimizing unit 510 receives an initial deposition condition and a target result of deposition that are input by the user 160. In inputting the received initial deposition condition into the first predicting unit 520, the optimizing unit 510 acquires a first predicted result of deposition (first result of deposition) output from the first predicting unit 520. The optimizing unit 510 also compares the first predicted result with the target result to thereby adjust the deposition condition. Further, in inputting the adjusted deposition condition into the first predicting unit 520, the optimizing unit 510 acquires a subsequent first predicted result of the deposition output from the first predicting unit 520, and then compares the subsequent first predicted result with the target result to thereby adjust the adjusted deposition condition.

Note that in the optimizing unit 510, (i) the comparing of a given first predicted result of deposition with the target result of deposition, and (ii) the adjusting of a given deposition condition based on a given compared result, are repeatedly performed, and thus a given deposition condition is optimized. For example, the optimizing unit 510 optimizes a given deposition condition while sequentially changing process data associated with each process data type, which is included in the given deposition condition.

Moreover, in the optimizing unit 510, when it is determined that a difference between a given first predicted result of deposition and a given target result of deposition meets a predetermined condition, an optimization process of the deposition condition is terminated. In this case, a given deposition condition adjusted when the optimization process is terminated is transmitted to the selector 550, as a first optimized deposition condition (first deposition condition).

Note that, for example, the above predetermined condition to be used in the optimizing unit 510 includes one of the following conditions (i), (ii), and (iii).

(i) A difference between the average thickness at n measurement points obtained from the first predicted result of deposition, and the average thickness at n measurement points obtained from the target result of deposition is less than or equal to a predetermined threshold.

(ii) Variation in the thickness at n measurement points obtained from the first predicted result of deposition is less than or equal to a predetermined threshold.

(iii) Another condition is adopted.

When any of (i), (ii), or (iii) above is met, the optimizing unit 510 determines that a difference between a given first predicted result of deposition and the target result of deposition meets a predetermined condition.

The first predicting unit 520 is an example of a first calculating unit, and has a trained linear model 521 generated by the first training unit 410 in the training phase. The first predicting unit 520 acquires a given initial deposition condition or an adjusted deposition condition, from the optimizing unit 510, and inputs the acquired initial deposition condition or adjusted deposition condition into the trained linear model 521. In response to inputting the initial deposition condition or adjusted deposition condition, the first predicting unit 520 transmits a given first predicted result of deposition output from the trained linear model 521, to the optimizing unit 510. Further, the first predicting unit 520 transmits, to the selector 550, a given first predicted result of deposition set upon determining that the predetermined condition described above is met.

Note that in the example illustrated in FIG. 5, until the predetermined condition is determined to be met by the optimizing unit 510, a given deposition condition is repeatedly adjusted in order to optimize the given deposition condition. However, when a given trained linear model is used, there are cases where a given deposition condition need not be repeatedly adjusted.

In a case where the deposition condition is not repeatedly adjusted, the optimizing unit 510 transmits a given first optimized condition of deposition to the selector 550, without determining whether the predetermined condition described above is met (or upon assuming that the difference between a given first predicted result of deposition and a given target result of deposition constantly meets the predetermined condition).

The optimizing unit 530 receives an initial deposition condition and a target result of deposition that are input by the user 160. In inputting the received initial deposition condition into the second predicting unit 540, the optimizing unit 530 acquires a second predicted result of deposition (second result of deposition) output from the second predicting unit 540. The optimizing unit 530 also compares the second predicted result with the target result to thereby adjust the deposition condition. Further, in inputting the adjusted deposition condition into the second predicting unit 540, the optimizing unit 530 acquires a subsequent second predicted result of deposition output from the second predicting unit 540, and then compares the subsequent second predicted result with the target result to thereby adjust the adjusted deposition condition.

Note that in the optimizing unit 530, (i) the comparing of a given second predicted result of deposition with the target result of deposition, and (ii) the adjusting of a given deposition condition based on a given compared result, are repeatedly performed, and thus a given deposition condition is optimized. For example, the optimizing unit 530 optimizes a given deposition condition while sequentially changing process data associated with each process data type, which is included in the given deposition condition.

In the optimizing unit 530, if it is determined that a difference between a given second predicted result of deposition and the target result of deposition meets a predetermined condition, the optimization process of the deposition condition is terminated. In this case, the given deposition condition adjusted when the optimization process is terminated is transmitted to the selector 550, as a second optimized deposition condition (second deposition condition).

Note that, for example, the predetermined condition to be used in the optimizing unit 530 includes one of the following conditions (i), (ii), and (iii).

(i) A difference between an average thickness at n measurement points obtained from the second predicted result of deposition, and an average thickness at n measurement points obtained from the target result of deposition is less than or equal to a predetermined threshold.

(ii) Variation in the thickness at n measurement points obtained from the second predicted result of deposition is less than or equal to a predetermined threshold.

(iii) Another condition is adopted.

When any of (i), (ii), or (iii) above is met, the optimizing unit 530 determines that a difference between a given second predicted result of deposition and the target result of deposition meets a predetermined condition.

When the condition described above is met, the optimizing unit 530 determines that a difference between a given second predicted result of deposition and the target result of deposition meets a predetermined condition.

The second predicting unit 540 is an example of a second calculating unit, and has a trained Gaussian process regression model 541 generated by the second training unit 420 in the training phase. The second predicting unit 540 acquires a given initial deposition condition or an adjusted deposition condition, from the optimizing unit 530, and inputs the acquired initial deposition condition or adjusted deposition condition into the trained Gaussian process regression model 541. In response to inputting the initial deposition condition or adjusted deposition condition, the second predicting unit 540 transmits a given second predicted result of deposition output from the trained Gaussian process regression model 541, to the optimizing unit 530. Further, the second predicting unit 540 transmits, to the selector 550, a given second predicted result of deposition set upon determining, by the optimizing unit 530, that the predetermined condition described above is met, as well as a transmitting width of a confidence interval (in this example, width of the confidence estimated from thicknesses at n measurement points) indicating variation of the given second predicted result.

The selector 550 outputs a given optimized deposition condition and a given predicted result of deposition. Specifically, the selector 550 selects one option from among (i) both the first optimized deposition condition, which is transmitted from the optimizing unit 510, and the first predicted result of deposition, which is transmitted from the first predicting unit 520, and (ii) both the second optimized deposition condition, which is transmitted from the optimizing unit 530, and the second predicted result of deposition, which is transmitted from the second predicting unit 540. The selector 550 outputs the selected one option. Note that the selector 550 selects the one option with reference to at least one of the following items.

(i) A width (which is estimated from thicknesses at n measurement points) of the confidence interval transmitted from the second predicting unit 540.

(ii) A result (which is obtained from thicknesses at n measurement points) obtained by comparing an absolute value indicative of the difference between a given first predicted result of deposition and the target result of deposition, with an absolute value of the difference between a given second predicted result of deposition and the target result of deposition. Where, the given first predicted result is transmitted from the first predicting unit 520, and the given second predicted result is transmitted from the second predicting unit 540.

In such a manner, the selector 550 refers to the width of a given confidence interval, as well as the absolute value of each of given differences, in order to determine whether prediction accuracy of the nonlinear regression model is decreased.

<Process for Outputting Deposition Condition>

Figure 6:
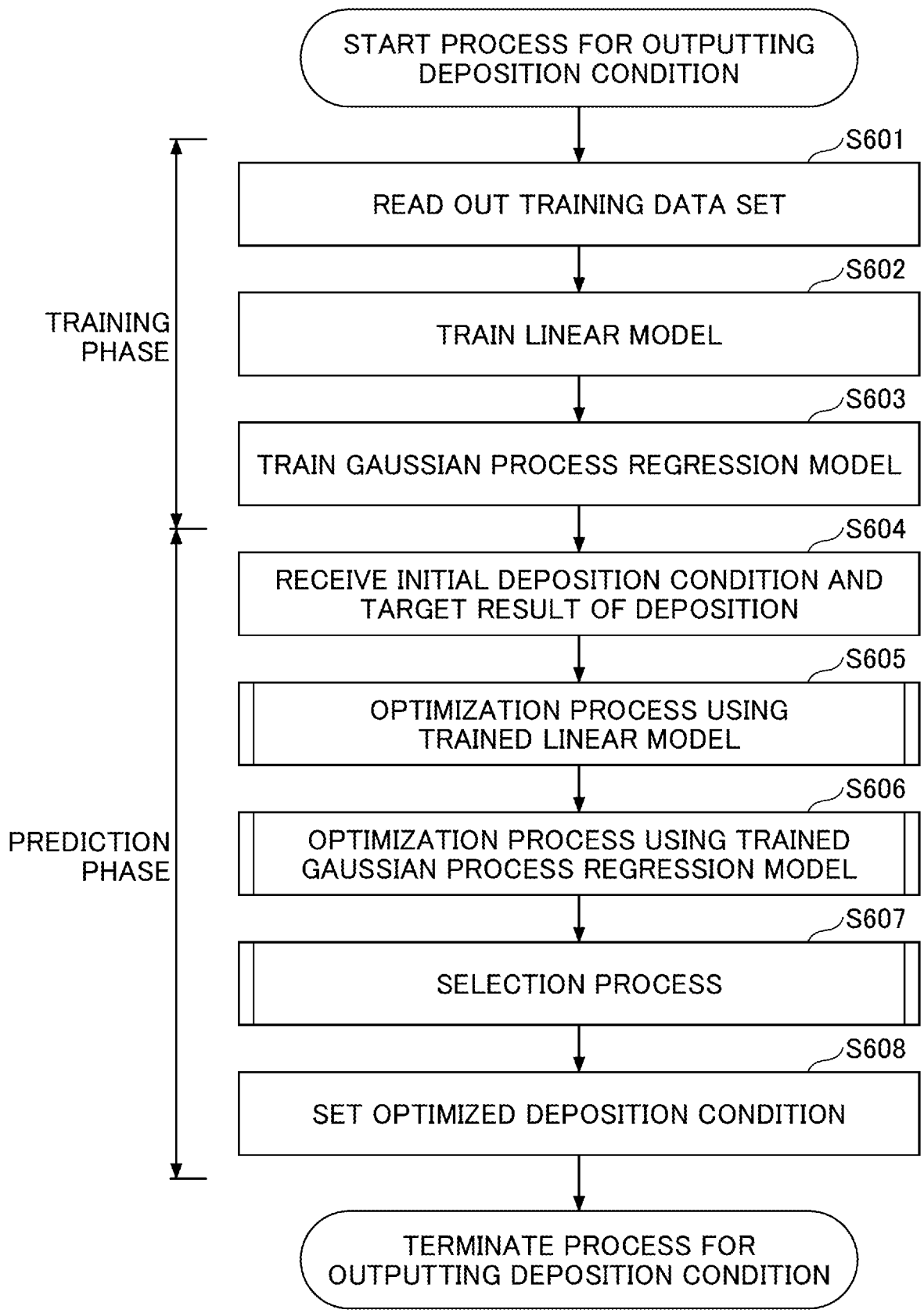
FIG. 6 is a flowchart illustrating an example of a process for outputting a deposition condition.

Hereafter, a flow of the process for outputting a deposition condition by the deposition-condition output device 140 will be described. FIG. 6 is an example of the flowchart illustrating an example of the process for outputting a deposition condition. Note that steps S601 to S603 are performed in the training phase.

In step S601, each of the first training unit 410 and the second training unit 420 retrieves a given training data set from the training-data set storage 141.

In step S602, the first training unit 410 uses the retrieved training data set to thereby perform a training process for a given linear model.

In step S603, the second training unit 420 uses the retrieved training data set to thereby perform a training process for a given Gaussian process regression model. When the training process is completed, the process transits to the prediction phase.

In step S604, each of the optimizing unit 510 and the optimizing unit 530 receives an initial deposition condition and a target deposition condition that are input by the user 160.

In step S605, the optimizing unit 510 and the first predicting unit 520 use a trained linear model to search for an optimum deposition condition (first optimized deposition condition). Note that the optimization process using the trained linear model will be described below in detail.

In step S606, the optimizing unit 530 and the second predicting unit 540 use a trained Gaussian process regression model to perform an optimization process of searching for an optimized deposition condition (second optimized deposition condition). Note that the optimization process using the trained Gaussian process regression model will be described below in detail.

In step S607, the selector 550 selects an optimized deposition condition and a predicted result of deposition, based on information, such as the width of a given confidence interval calculated when the second predicting unit 540 searches for the second optimized deposition condition. Note that the selection process will be described below in detail.

In step S608, the selector 550 provides the user 160 with the selected optimized deposition condition and predicted result of deposition. The selector 550 also sets the selected optimized deposition condition in the deposition apparatus 120.

<Details of Processing for Outputting Deposition Condition>

For steps relating to the process for outputting a deposition condition, step S605 in which the optimization process is performed using the trained linear model, step S606 in which the optimization process is performed using the trained Gaussian process regression model, and step S607 in which the selection process is performed, will be hereafter described in detail.

(1) Details of the Optimization Process Using the Trained Linear Model (Step S605)

Figure 7:
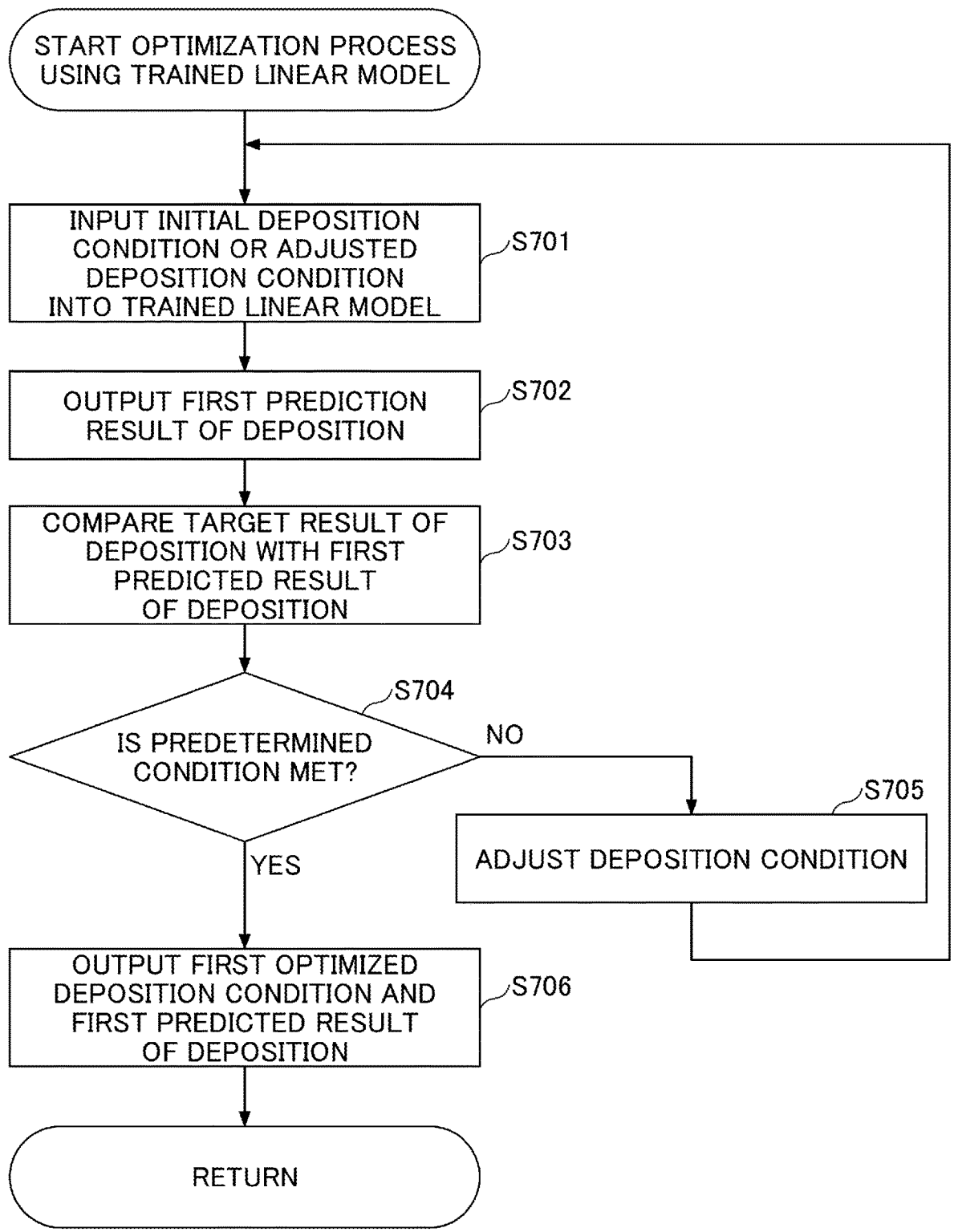
FIG. 7 is a flowchart illustrating an example of an optimization process using a trained linear model.

FIG. 7 is a flowchart illustrating an example of the optimization process using the trained linear model.

In step S701, the first predicting unit 520 inputs the initial deposition condition or the adjusted deposition condition, into the trained linear model 521. The initial deposition condition or the adjusted deposition condition to be input is transmitted by the optimizing unit 510.

In step S702, the first predicting unit 520 transmits the first predicted result of deposition output from the trained linear model 521, to the optimizing unit 510.

In step S703, the optimizing unit 510 compares the target result of deposition with the first predicted result of deposition.

In step S704, the optimizing unit 510 determines whether a compared result meets a predetermined condition. In step S704, if it is determined that the predetermined condition is not met (NO in step S704), the process proceeds to step S705.

In step S705, the optimizing unit 510 adjusts the deposition condition and then transmits the adjusted deposition condition to the first predicting unit 520. Then, the process returns to step S701.

In contrast, in step S704, if a predetermined condition is determined to be met (YES in step S704), the process proceeds to step S706. Note that as described above, when a given deposition condition need not be repeatedly adjusted using the trained linear model, the process proceeds to step S706 without performing the process in step S704 (or upon an assumption that the predetermined condition is constantly met).

In step S706, the optimizing unit 510 transmits the first optimized deposition condition to the selector 550, and the first predicting unit 520 transmits a corresponding first predicted result of deposition to the selector 550. Then, the process returns to step S606 in FIG. 6.

(2) Details of Optimization Process Using Trained Gaussian Process Regression Model (Step S606)

Figure 8:
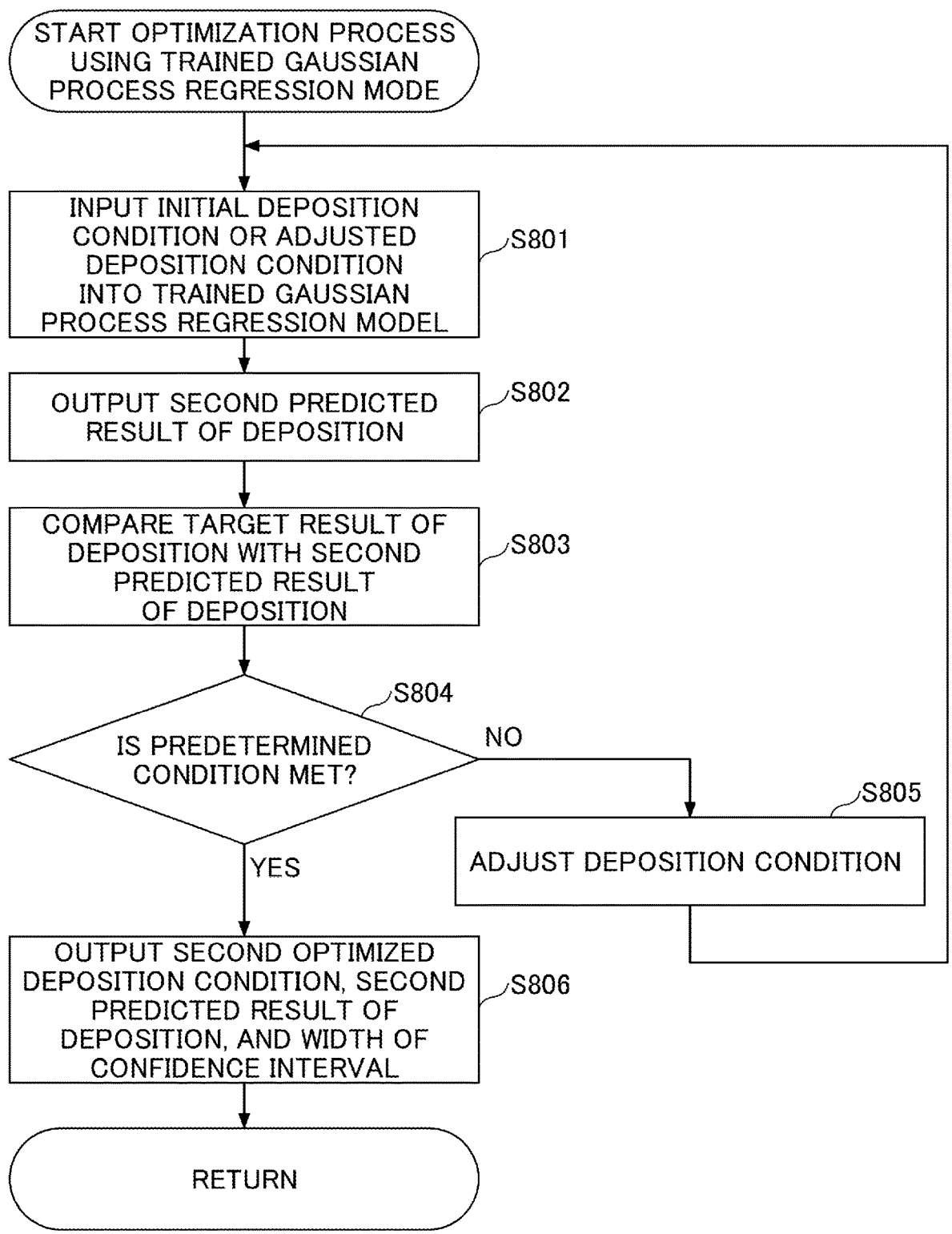
FIG. 8 is a flowchart illustrating an example of an optimization process using a trained Gaussian process regression model.

FIG. 8 is a flowchart illustrating an example of the optimization process using the trained Gaussian process regression model.

In step S801, the second predicting unit 540 inputs the initial deposition condition or the adjusted deposition condition, into the trained Gaussian process regression model 541. The initial deposition condition or the adjusted deposition condition to be input is transmitted by the optimizing unit 530.

In step S802, the second predicting unit 540 transmits the second predicted result of deposition output from the trained Gaussian process regression model 541, to the optimizing unit 530.

In step S803, the optimizing unit 530 compares the target result of deposition with the second predicted result of deposition.

In step S804, the optimizing unit 530 determines whether a compared result meets a predetermined condition. In step S804, if a predetermined condition is determined not to be met (NO in step S804), the process proceeds to step S805.

In step S805, the optimizing unit 530 adjusts the deposition condition and then transmits the adjusted deposition condition to the second predicting unit 540. Then, the process returns to step S801.

In contrast, in step S804, if a predetermined condition is determined to be met (YES in step S804), the process proceeds to step S806.

In step S806, the optimizing unit 530 transmits the second optimized deposition condition to the selector 550, and the second predicting unit 540 transmits, to the selector 550, the second predicted result of deposition and the width of the confidence interval. Then, the process returns to step S607 in FIG. 6.

(3) Details of Selection Process (Step S607)

Figure 9:
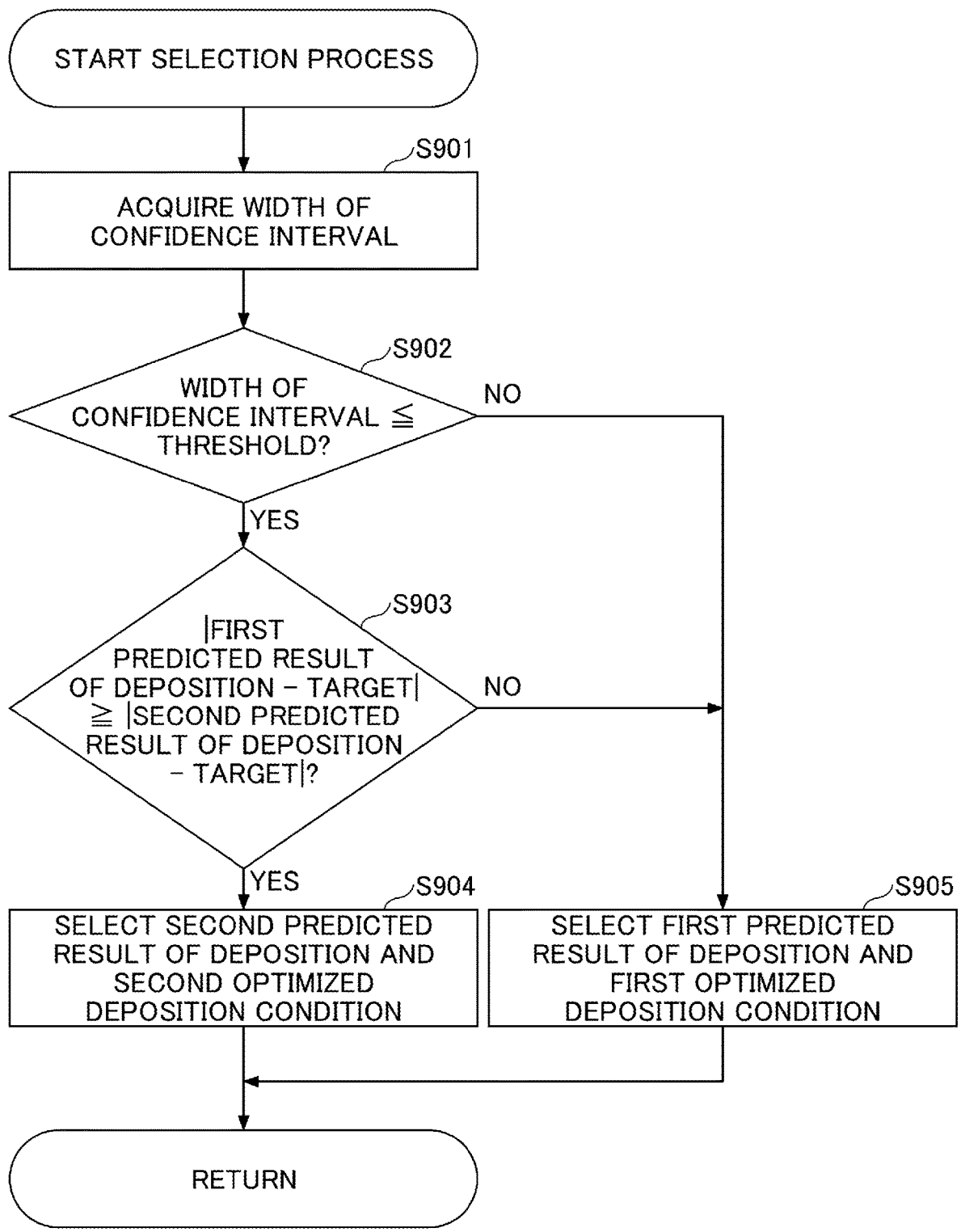
FIG. 9 is a flowchart illustrating an example of a selection process.

FIG. 9 is a flowchart illustrating an example of the selection process. In step S901, the selector 550 acquires the width (which is estimated from thicknesses at n measurement points) of the confidence interval transmitted from the second predicting unit 540.

In step S902, the selector 550 determines whether the acquired width of the confidence interval meets a predetermined condition (for example, it is determined whether the width is less than or equal to a predetermined threshold). In step S902, if it is determined that the width of the confidence interval does not meet a predetermined condition (No in step S902), the process proceeds to step S905. In this example, it is determined that the width is greater than a predetermined threshold. Note that when the process proceeds to step S905, the selector 550 determines that (i) a given width of the confidence interval estimated from thicknesses at n measurement points is greater than a predetermined threshold, or (ii) a given width of the confidence interval estimated from a predetermined number of thicknesses, among thicknesses at n measurement points, is greater than a predetermined threshold.

In contrast, in step S902, if it is determined that the width of the confidence interval meets a predetermined condition (for example, the width is less than or equal to a predetermined threshold), the process proceeds to step S903.

In step S903, the selector 550 calculates an absolute value (absolute value of a first difference) of a difference between the first predicted result of deposition, which is transmitted by the first predicting unit 520, and the target result of deposition. For example, the selector 550 calculates, as the absolute value of the first difference, the sum of the squares of the difference between the first predicted result of deposition, which is calculated from thicknesses at n measurement points, and the target result of deposition.

The selector 550 calculates an absolute value (absolute value of a second difference) of a difference between the second predicted result of deposition, which is transmitted by the second predicting unit 540, and the target result of deposition. For example, the selector 550 calculates, as the absolute value of the second difference, the sum of the squares of the difference between the second predicted result of deposition, which is calculated from thicknesses at n measurement points, and the target result of deposition.

Further, the selector 550 determines whether the absolute value of the first difference is greater than or equal to the absolute value of the second difference.

In step S903, if it is determined that the absolute value of the first difference is less than the absolute value of the second difference (NO in step S903), the process proceeds to step S905.

In step S905, the selector 550 selects the first predicted result of deposition and the first optimized film deposition condition, where the first predicted result of deposition is transmitted by the first predicting unit 520.

In contrast, in step S903, if it is determined that the absolute value of the first difference is the greater than or equal to the absolute value of the second difference (YES in step S903), the process proceeds to step S904.

In step S904, the selector 550 selects the second predicted result of deposition and the second optimized deposition condition, where the second predicted result of deposition is transmitted by the second predicting unit 540.

Specific Examples of Selection Process

Figure 10A:
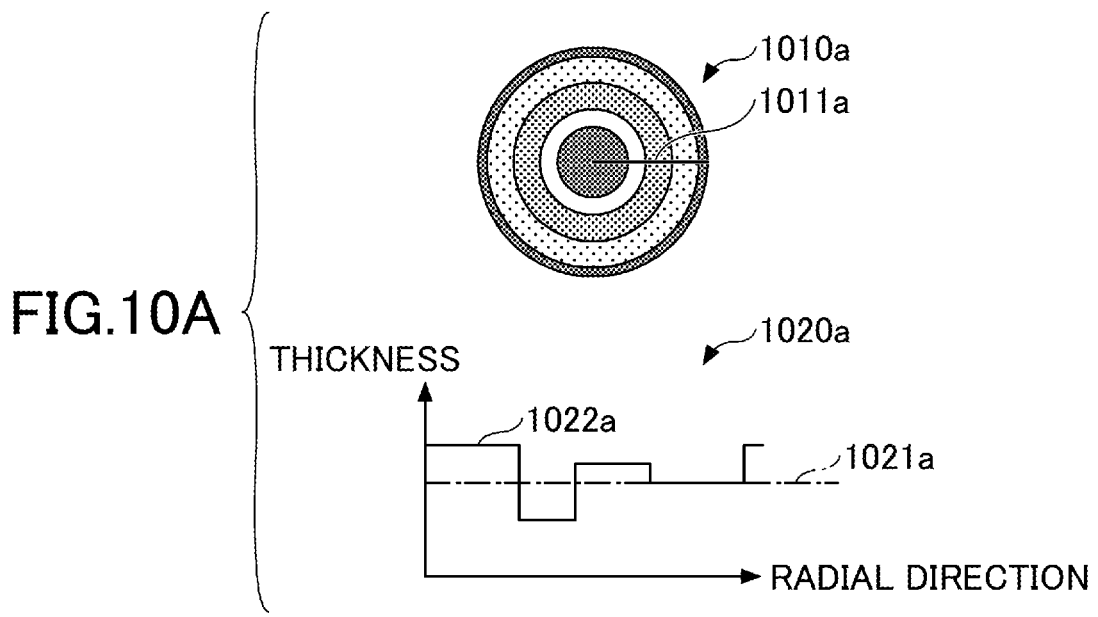
FIGS. 10A to 10F are diagrams illustrating a specific example of the selection process.

Hereafter, specific examples of the selection process will be described. FIGS. 10A to 10F are diagrams illustrating a specific example of the selection process. Each of FIGS. 10A to 100 illustrates a given first predicted result of deposition obtained when a given first optimized deposition condition was calculated using the trained linear model 521. In each of FIGS. 10A to 100, a given wafer 1010a is schematically represented as the processed wafer 130, and different shading indicates variation in the film thickness. The film thickness 1020a indicates a given thickness along a radius 1011a of a given wafer. The single dotted line 1021a represents a given target result of deposition, and the solid line 1022a represents a given first predicted result of deposition.

Figure 10B:
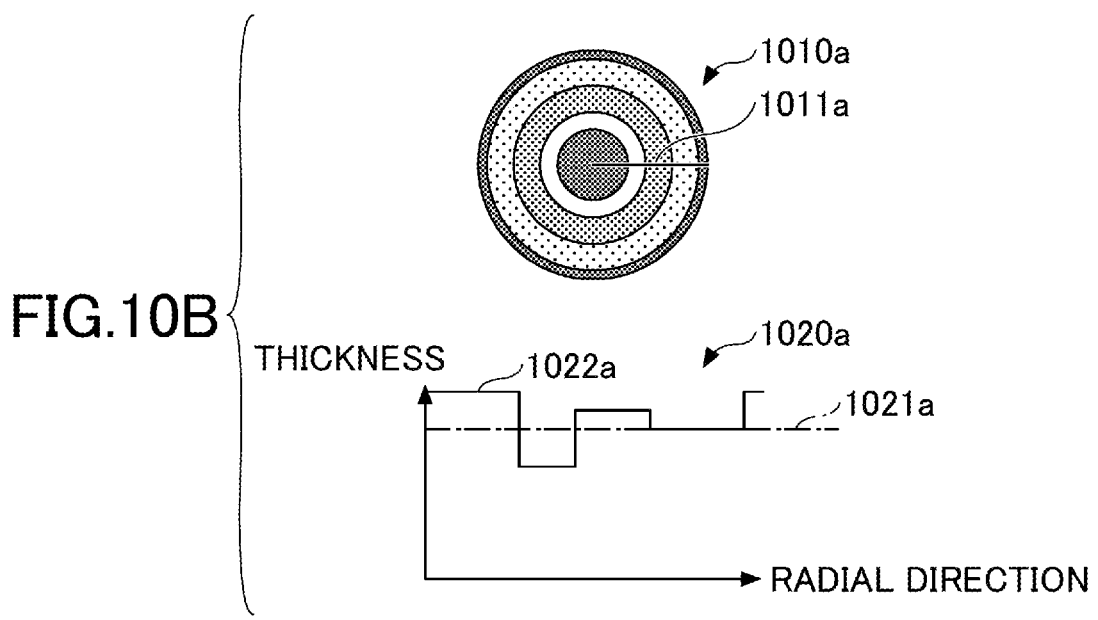
Figure 10C:
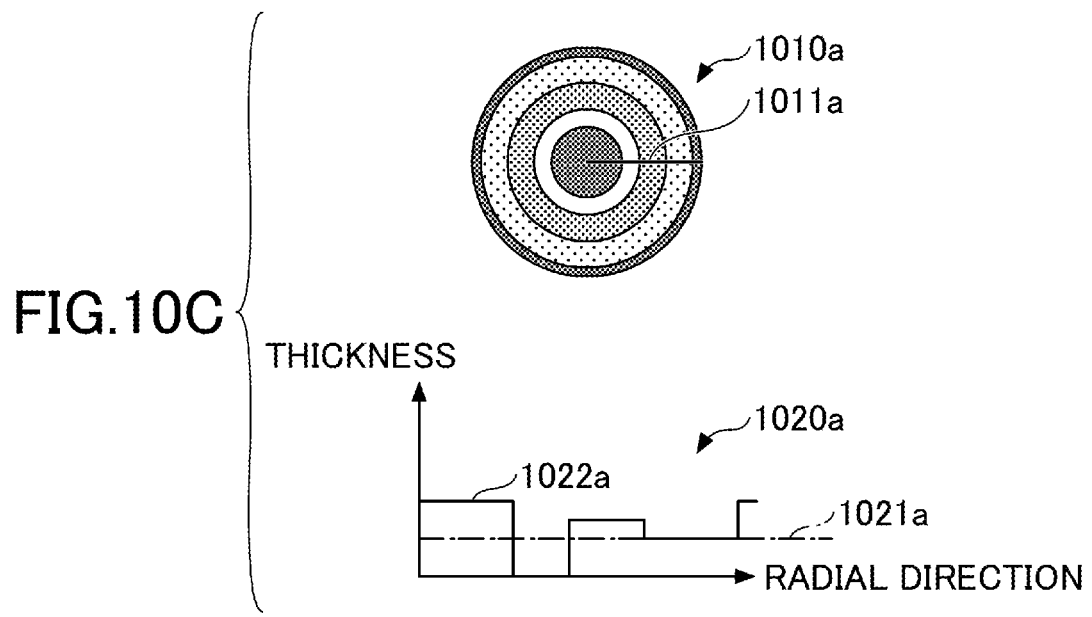
Figure 10D:
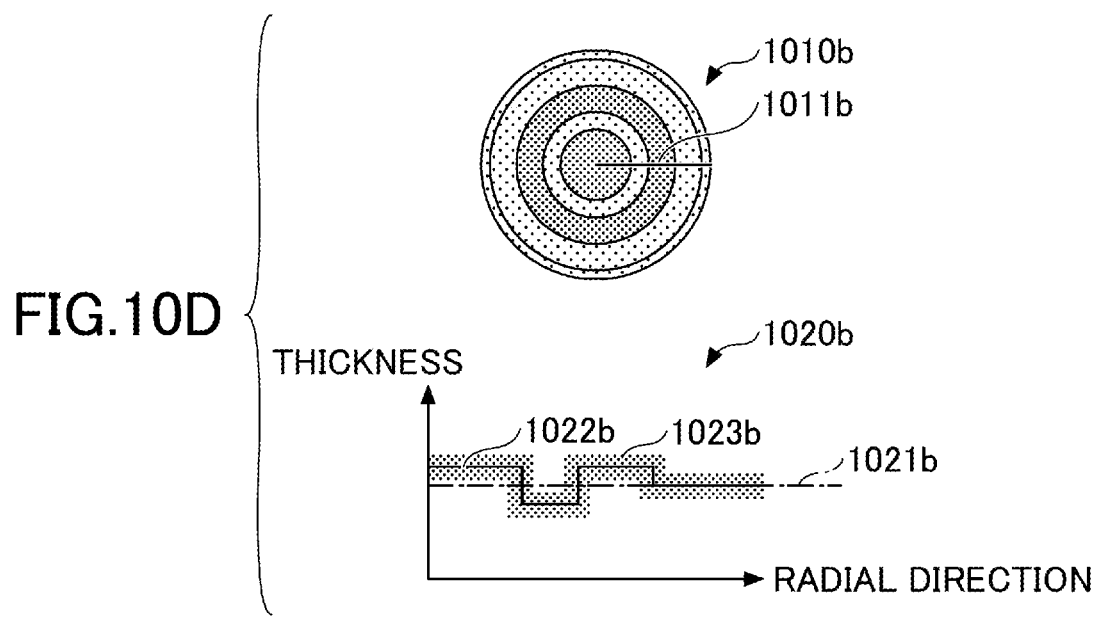
Figure 10E:
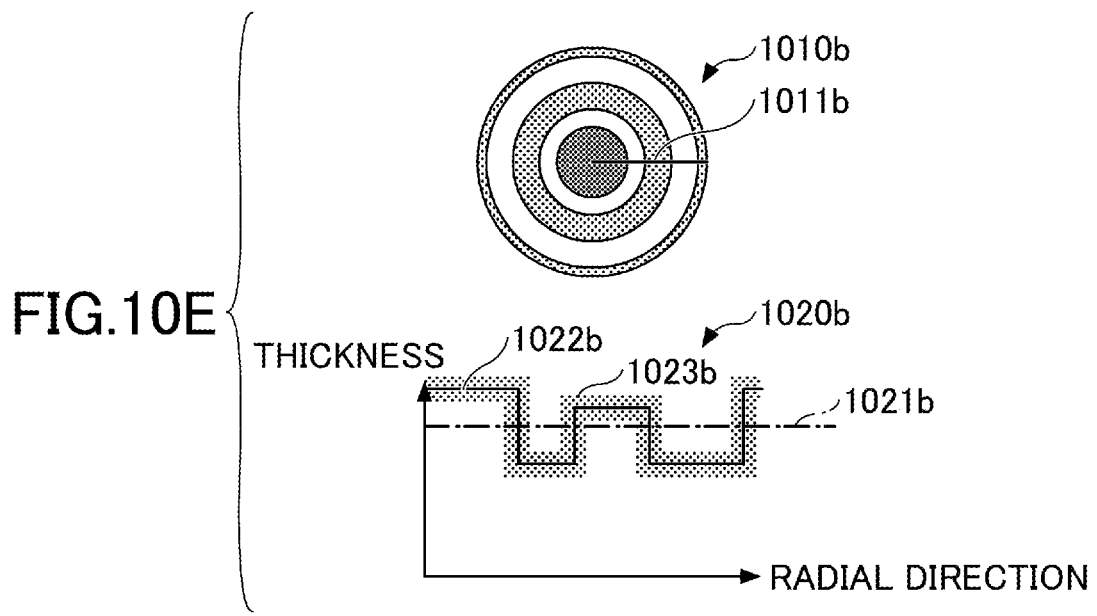
Figure 10F:
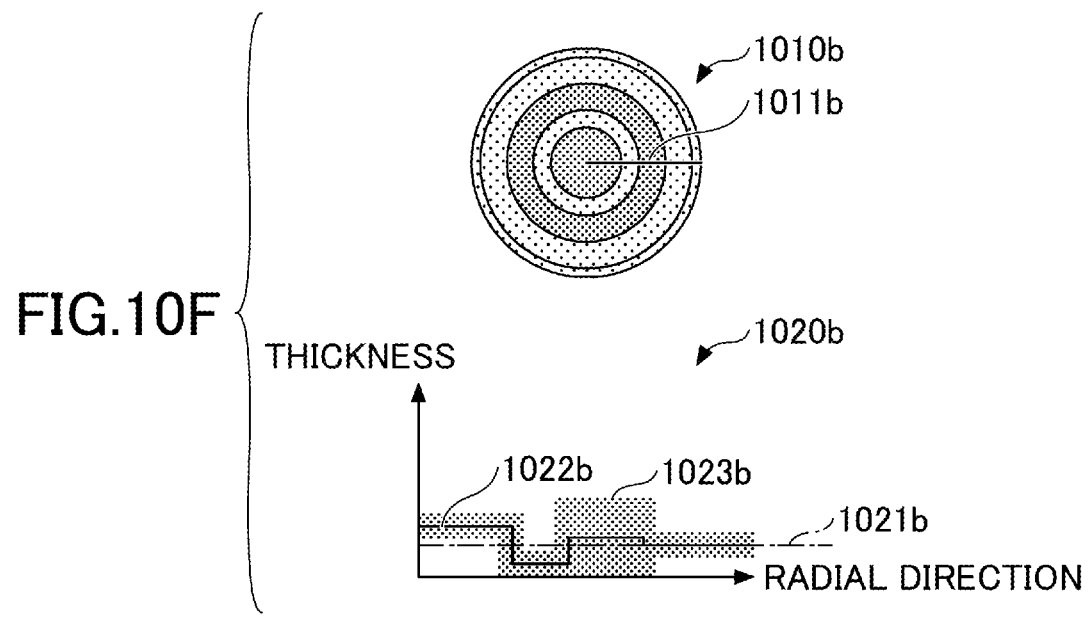

Each of FIG. 10D to 10F illustrates a given second predicted result of deposition obtained when a given second optimized deposition condition was calculated using the trained Gaussian process regression model 541. In each of FIGS. 10D to 10F, a given wafer 1010b is schematically represented as the processed wafer 130, and different shading indicates variation in the thickness. The thickness 1020b indicates a given thickness along a radius 1011b of a given wafer. The single dotted line 1021b represents a given target result of deposition, and the solid line 1022b represents a given second predicted result of deposition, and the hatching 1023b indicates a given width of the confidence interval.

FIG. 10A to FIG. 10D illustrate the selection process when the same initial deposition condition and the same target deposition condition are input in the prediction phase. In this case, in step S902, the selector 550 determines that the width of a given confidence interval is less than or equal to a threshold. In step S903, the selector 550 determines that the condition of |first predicted result of deposition−target result of deposition|≥|second predicted result of deposition−target result of deposition|) is met. Thus, the selector 550 selects the second predicted result of deposition (predicted result 1020b).

FIG. 10B and FIG. 10E illustrate the selection process when the same initial deposition condition and the same target deposition condition were inputted in the prediction phase, where the initial deposition condition and the target deposition condition are different from the initial deposition condition and the target deposition condition used in FIGS. 10A and 10D. In this case, in step S902, the selector 550 determines that the width of a given confidence interval is less than or equal to a threshold. In step S903, the selector 550 determines that the condition of |first predicted result of deposition−target result of deposition|<|second predicted result of deposition−target result of deposition| is met. Thus, the selector 550 selects the first predicted result of deposition (predicted result 1020a).

FIG. 10C and FIG. 10F illustrate the selection process when the same initial deposition condition and the same target deposition condition were input in the prediction phase, where the initial deposition condition and the target deposition condition are different from the initial deposition conditions and the target deposition conditions used in FIGS. 10A, 10B, 10D, and 10E. In this case, in step S902, the selector 550 determines that the width of a given confidence interval is greater than a threshold. Thus, the selector 550 selects the first predicted result of deposition (predicted result 1020a).

Thus, when the trained Gaussian process regression model 541 is used, prediction accuracy may be decreased depending on a given initial deposition condition and a given target result of deposition, in comparison to the case where the trained linear model 521 is used. In view of the problem described above, the selector refers to the width of a given confidence interval and the absolute value of each of given differences. Accordingly, the selector 550 can output the appropriately optimized deposition condition and predicted result of deposition.

SUMMARY

As seen from the above description, the deposition-condition output device according to the first embodiment uses a given linear model in which the deposition process by the deposition apparatus is modeled, to thereby calculate a given first optimized deposition condition under which a given target result of deposition is obtained. The deposition-condition output device also uses a given Gaussian process regression model in which the deposition process by the deposition apparatus is modeled, to thereby calculate a given second optimized deposition condition under which the given target result of deposition is obtained.

Moreover, the deposition-condition output device selects one from among the first optimized deposition condition and the second optimized deposition condition, on the basis of whether the width of a given confidence interval of a given predicted result of deposition being estimated when the second optimized deposition condition is calculated meets a predetermined condition. Then, the deposition-condition output device outputs a selected deposition condition.

Thus, according to the first embodiment, a deposition-condition output device can be provided in which an appropriate deposition condition can be output.

Second Embodiment

The first embodiment has been described using an example in which the Gaussian process regression model is used as a nonlinear regression model. However, the nonlinear regression model is not limited to Gaussian process regression models. Other nonlinear regression models may be used as long as they are suitable for calculating a given predicted result and a confidence interval of the given predicted result.

The first embodiment has been described using an example in which a given program to cause a computer to output a deposition condition is installed in the deposition-condition output device 140. In other words, the deposition-condition output device 140 is separated from the deposition apparatus 120. However, the given program to cause a computer to output a deposition condition is stored in a memory and the memory may be provided in the deposition apparatus 120. In this case, the given program is executed by the deposition apparatus 120 and thus the deposition apparatus 120 may serve as the deposition-condition output device.

While certain embodiments have been described, these embodiments have been presented by way of example only, and are not intended to limit the scope of the disclosures. Indeed, the embodiments described herein may be embodied in a variety of other forms. Furthermore, various omissions, substitutions and changes in the form of the embodiments described herein may be made without departing from the spirit of the disclosures. The accompanying claims and their equivalents are intended to cover such forms or modifications as would fall within the scope and spirit of the disclosures.

According to the present disclosure, a deposition-condition output device, a method for outputting a deposition condition, and a recording medium for determining and outputting appropriate deposition conditions are provided.

What is claimed is:

1. A deposition-condition output device comprising:
a processing circuit configured to:
train a linear regression model applied to a deposition process that a deposition apparatus performs, to optimize a first deposition condition under which a target result of deposition is obtained based on the trained linear regression model;
train a nonlinear regression model applied to the deposition process that the deposition apparatus performs, to optimize a second deposition condition under which the target result of the deposition is obtained based on the trained nonlinear regression model;
compare a width of a confidence interval of a deposition result that is estimated under the optimized second deposition condition, with a threshold; and
select, as a candidate condition under which a given learning model among the linear regression model and the nonlinear regression model estimates a deposition result, at least one of the optimized first deposition condition or the optimized second deposition condition based on a result of comparison of the width of the confidence interval with the threshold, such that the deposition apparatus processes a substrate based on the selected candidate condition,
wherein upon determining that the width of the confidence interval is less than or equal to the threshold, the processing circuit is configured to:
compare a first difference between a first result of the deposition and the target result of the deposition, with a second difference between a second result of the deposition and the target result of the deposition, the first result of the deposition being obtained under the optimized first deposition condition, and the second result of the deposition being obtained under the optimized second deposition condition;
select one deposition condition from the first deposition condition and the second deposition condition, based on a result of comparison of the first difference with the second difference; and
output the selected deposition condition to an external device, and
wherein the deposition-condition output device causes the deposition apparatus to process the substrate based on the selected deposition condition.

2. The deposition-condition output device according to claim 1, wherein the processing circuit is configured to select, upon determining that the width of the confidence interval is greater than the threshold, the first deposition condition, and to output the first deposition condition to an external device.

3. The deposition-condition output device according to claim 1, wherein the processing circuit is configured to select the first deposition condition, and to output the selected first deposition condition to the external device, upon determining that the first difference is less than the second difference; and
select the second deposition condition, and to output the selected second deposition condition to the external device, upon determining that the first difference is greater than or equal to the second difference.

4. The deposition-condition output device according to claim 1, wherein each of the linear model and the nonlinear regression model is a trained model of which one or more model parameters are updated such that, under an input deposition condition, a corresponding predicted result of the deposition approaches the target result of the deposition.

5. The deposition-condition output device according to claim 1, wherein the processing circuit is configured to determine one of the linear regression model and the nonlinear regression model based on the result of comparison of the width of the confidence interval with the threshold, the one regression model being used to estimate the deposition result.

6. A method for outputting a deposition condition, the method comprising:
training a linear regression model applied to a deposition process that a deposition apparatus performs, to optimize a first deposition condition under which a target result of deposition is obtained based on the trained linear regression model;
train a nonlinear regression model applied to the deposition process that the deposition apparatus performs, to optimize a second deposition condition under which the target result of the deposition is obtained based on the trained nonlinear regression model;
comparing a width of a confidence interval of a deposition result that is estimated under the optimized second deposition condition, with a threshold;
selecting, as a candidate condition under which a given learning model among the linear regression model and the nonlinear regression model estimates a deposition result, at least one of the optimized first deposition condition or the optimized second deposition condition based on a result of comparison of the width of the confidence interval with the threshold, such that the deposition apparatus processes a substrate based on the selected candidate condition; and
causing the deposition apparatus to process the substrate based on the selected deposition condition,
wherein the method further includes
comparing, upon determining that the width of the confidence interval is less than or equal to the threshold, a first difference between a first result of the deposition and the target result of the deposition, with a second difference between a second result of the deposition and the target result of the deposition, the first result of the deposition being obtained under the optimized first deposition condition, and the second result of the deposition being obtained under the optimized second deposition condition;
selecting one deposition condition from the first deposition condition and the second deposition condition, based on a result of comparison of the first difference with the second difference; and
outputting the selected deposition condition to an external device.

7. A non-transitory recording medium storing a program that, when executed by a computer, causes the computer to perform a method, the method comprising:
training a linear regression model applied to a deposition process that a deposition apparatus performs, to optimize a first deposition condition under which a target result of deposition is obtained based on the trained linear regression model;

training a nonlinear regression model applied to the deposition process that the deposition apparatus performs, to optimize a second deposition condition under which the target result of the deposition is obtained based on the trained nonlinear regression model;

comparing a width of a confidence interval of a deposition result that is estimated under the optimized second deposition condition, with a threshold;

selecting, as a candidate condition under which a given learning model among the linear regression model and the nonlinear regression model estimates a deposition result, at least one of the optimized first deposition condition or the optimized second deposition condition based on a result of comparison of the width of the confidence interval with the threshold, such that the deposition apparatus processes a substrate based on the selected candidate condition; and causing the deposition apparatus to process the substrate based on the selected deposition condition, wherein the method further includes comparing, upon determining that the width of the confidence interval is less than or equal to the threshold, a first difference between a first result of the deposition and the target result of the deposition, with a second difference between a second result of the deposition and the target result of the deposition, the first result of the deposition being obtained under the optimized first deposition condition, and the second result of the deposition being obtained under the optimized second deposition condition;

selecting one deposition condition from the first deposition condition and the second deposition condition, based on a result of comparison of the first difference with the second difference; and outputting the selected deposition condition to an external device.

8. A deposition apparatus comprising:

a memory storing the program according to claim 7; and a processor electrically coupled to the memory, the processor being configured to execute the program.

\* \* \* \* \*